US012622962B2

(12) United States Patent
Li et al.

(10) Patent No.: US 12,622,962 B2
(45) Date of Patent: May 12, 2026

(54) PHARMACEUTICAL COMPOSITION AND USE THEREOF

(71) Applicant: Grand Theravac Life Sciences (Nanjing) Co., Ltd., Nanjing (CN)

(72) Inventors: Jianqiang Li, Nanjing (CN); Jun Ge, Nanjing (CN); Jiaojiao Sun, Nanjing (CN); Tong Zhou, Nanjing (CN); Sulin Ren, Nanjing (CN); Changyao Tan, Nanjing (CN); Yue Gu, Nanjing (CN); Hongying Huang, Nanjing (CN); Shiwei Wang, Nanjing (CN); Xiaoxiao Chen, Nanjing (CN); Jingfeng Huang, Nanjing (CN); Xaiodong Wang, Nanjing (CN); Yue Chen, Nanjing (CN)

(73) Assignee: Grand Theravac Life Sciences (Nanjing) Co., Ltd., Nanjing (CN)

( * ) Notice: Subject to any disclaimer, the term of this patent is extended or adjusted under 35 U.S.C. 154(b) by 1004 days.

(21) Appl. No.: 17/784,081

(22) PCT Filed: Dec. 11, 2020

(86) PCT No.: PCT/CN2020/135570
§ 371 (c)(1),
(2) Date: Jun. 9, 2022

(87) PCT Pub. No.: WO2021/115408
PCT Pub. Date: Jun. 17, 2021

(65) Prior Publication Data
US 2023/0073321 A1    Mar. 9, 2023

(30) Foreign Application Priority Data
Dec. 13, 2019    (CN) .......................... 201911279536.0

(51) Int. Cl.
*A61K 39/39* (2006.01)
*A61K 31/711* (2006.01)
(Continued)

(52) U.S. Cl.
CPC ............ *A61K 39/39* (2013.01); *A61K 31/711* (2013.01); *A61K 39/245* (2013.01); *A61K 39/29* (2013.01);
(Continued)

(58) Field of Classification Search
None
See application file for complete search history.

(56) References Cited

U.S. PATENT DOCUMENTS 6,544,518 B1    4/2003  Friede et al.
7,049,302 B1    5/2006  Kensil
(Continued)

FOREIGN PATENT DOCUMENTS

CN        1372473 A    10/2002
CN        1468256 A     1/2004
(Continued)

OTHER PUBLICATIONS

Google translation of Chen et al. CN 104873969, Jun. 19, 2018.*
(Continued)

*Primary Examiner* — Shanon A. Foley
(74) *Attorney, Agent, or Firm* — Christensen O'Connor Johnson Kindness PLLC

(57)    ABSTRACT
The present invention belongs to the field of biopharmaceutics and in particular relates to a pharmaceutical composition. The pharmaceutical composition comprises a hepatitis B surface antigen, a hepatitis B core antigen, and an immunostimulatory composition, wherein the immunostimulatory composition comprises a saponin and a CpG oligode-
(Continued)

oxynucleotide, or consists of an adjuvant comprising a saponin and a CpG oligodeoxynucleotide.

18 Claims, 7 Drawing Sheets

Specification includes a Sequence Listing.

(51) Int. Cl.

| | | |
|---|---|---|
| *A61K 39/245* | (2006.01) | |
| *A61K 39/29* | (2006.01) | |
| *A61P 31/04* | (2006.01) | |
| *A61P 31/12* | (2006.01) | |
| *A61P 31/22* | (2006.01) | |
| *C07K 16/28* | (2006.01) | |
| *A61K 39/00* | (2006.01) | |

(52) U.S. Cl.
CPC ............ *A61K 39/292* (2013.01); *A61P 31/04* (2018.01); *A61P 31/12* (2018.01); *A61P 31/22* (2018.01); *C07K 16/2803* (2013.01); *A61K 2039/55561* (2013.01); *A61K 2039/55577* (2013.01)

(56) References Cited

U.S. PATENT DOCUMENTS

| | | | | |
|---|---|---|---|---|
| 9,878,035 | B2 * | 1/2018 | Du | .......................... A61P 31/20 |
| 2008/0199487 | A1 | 8/2008 | Galli | |
| 2011/0059132 | A1 | 3/2011 | Melber et al. | |
| 2023/0073321 | A1 * | 3/2023 | Li | .......................... A61P 31/12 |

FOREIGN PATENT DOCUMENTS

| | | | |
|---|---|---|---|
| CN | 101309931 | A | 11/2008 |
| CN | 101979566 | A | 2/2011 |
| CN | 104043120 | A | 9/2014 |
| CN | 104873969 | A | 9/2015 |
| CN | 107249629 | A | 10/2017 |
| CN | 109154004 | A | 1/2019 |
| CN | 111346223 | A | 6/2020 |
| CN | 111420043 | A | 7/2020 |
| CN | 112972670 | A | 6/2021 |
| TW | 1232753 | B | 5/2005 |
| TW | 1674269 | B | 10/2019 |
| WO | 0009159 | A1 | 2/2000 |
| WO | 0151083 | A2 | 7/2001 |
| WO | 2007/031334 | A2 | 3/2007 |

OTHER PUBLICATIONS

SEQ 1 alignment with Geneseq db access No. BCM91341 by Chen et al. in CN104873969 Sep. 2015.*

SEQ 2 alignment with Geneseq db access No. BCM91343 by Chen et al. in CN104873969 Sep. 2015.*

Ishikawa (Nagoya Journal of Medical Science. Aug. 2012; 74 (3-4): 217).*

Javanbakht et al. (Molecular Therapy Nucleic Acids. Jun. 1, 2018; 11: 441-454).*

Extended European Search Report mailed on Aug. 5, 2024, issued in European Application No. 20897828.8; 10 pages.

Chinese Search Report mailed on Sep. 23, 2023, issued in Chinese Application No. 2020114595003; 3 pages.

Search Report mailed May 15, 2024, issued in corresponding Application No. TW 109143766, filed Dec. 11, 2020, 3 pages.

Office Action mailed May 2, 2024, issued in corresponding Vietnamese Application No. 1-2022-04416, filed Dec. 11, 2020, 4 pages.

Written Opinion mailed on Mar. 10, 2021, issued in corresponding International Application No. PCT/CN2020/135570 filed Dec. 11, 2020, 6 pages.

International Search Report mailed on Mar. 10, 2021, issued in corresponding International Application No. PCT/CN2020/135570 filed Dec. 11, 2020, 6 pages.

Chen et al., "The new therapeutic vaccine of hepatitis B can induce cellular and humoral immune responses without tolerance," Prog in Microbiol Immunol, 41(6), Dec. 2013, 2 pages.

Yu et al., "Requirement of nucleobase proximal to CpG dinucleotide for immunostimulatory activity of synthetic CpG DNA," Bioorganic & Medicinal Chemistry, 11(3): 459-464, 2003, (Abstract only), 1 page.

Min, Seo Jeong, "Immunostimulatory Activity of Specific CpG Oligonucleotides from Bifidobacterium longum Genome on RAW 264.7 Macrophage Cells," Journal of the Korean Society for Applied Biological Chemistry, 52(5): pp. 525-530, 2009, (Abstract only, 1 page).

Pirahmadi et al., "Combining MPL, CpG ODN, and QS-21 adjuvants induce strong and persistent functional antibodies and T cell responses against cell-traversal protein for ookinettes and sporozoites (CelTOS) of Plasmodium falciparum in BALB/c mice," American Society for Microbiology, Apr. 1, 2019, 58 pages.

* cited by examiner

SEQUENCE LISTING

<160> NUMBER OF SEQ ID NOS: 32

<210> SEQ ID NO 1
<211> LENGTH: 226
<212> TYPE: PRT
<213> ORGANISM: Artificial Sequence
<220> FEATURE:
<223> OTHER INFORMATION: Synthetic

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
            35                  40                  45

Leu Gly Gln Asn Ser Gln Ser Pro Thr Ser Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
            195                 200                 205

Val Ser Pro Phe Ile Pro Leu Leu Pro Ile Phe Phe Cys Leu Trp Val
        210                 215                 220

Tyr Ile
225

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

-continued

```
Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
            165                 170                 175

Gln Ser Arg Glu Ser Gln Cys
            180

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
tgactgtgaa cgttcgagat ga                                        22

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tcgtcgtttt gtcgttttgt cgtt                                      24

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tccatgacgt tcctgacgtt                                           20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tcgttcgttc gttcgttcgt t                                         21

<210> SEQ ID NO 7
<211> LENGTH: 25
<212> TYPE: DNA
<213> ORGANISM: Artificial Sequence
<220> FEATURE:
<223> OTHER INFORMATION: Synthetic
```

-continued

```
<400> SEQUENCE: 7
tcgttcgttc gttcgttcgt tcgtt                                     25

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
tcgtcgtcgt cgtcgtcgtc g                                         21

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
tcgacgttcg tcgttcgtcg ttc                                       23

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tccatgacgt tcctgatgct                                           20

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
tgtcgtcgtc gtttgtcgtt tgtcgtt                                   27

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12 ggggacgat cgtcggggg                                             20

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggggacgacg tcgtgggggg g                                         21

<210> SEQ ID NO 14
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 14
tcgtcgtttc gcgcgcgccg                                                        20

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
tcgtcgttcg ttcgtcgaac gacgtttgat                                             30

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Ser Pro His His Thr Ala Leu Arg Gln Ala Ile Leu Cys Trp Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Thr Ala Leu Arg Gln Ala Ile Leu Cys Trp Gly Glu Leu Met Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Gln Ala Ile Leu Cys Trp Gly Glu Leu Met Asn Leu Ala Thr Trp
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Cys Trp Gly Glu Leu Met Asn Leu Ala Thr Trp Val Gly Ser Asn
1               5                   10                  15

<210> SEQ ID NO 20
<211> LENGTH: 15
<212> TYPE: PRT
<213> ORGANISM: Artificial Sequence
```

-continued

```
<220> FEATURE:
<223> OTHER INFORMATION: Synthetic

<400> SEQUENCE: 20

Leu Met Asn Leu Ala Thr Trp Val Gly Ser Asn Leu Glu Asp Pro
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Ala Thr Trp Val Gly Ser Asn Leu Glu Asp Pro Ala Ser Arg Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Gly Ser Asn Leu Glu Asp Pro Ala Ser Arg Glu Leu Val Val Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Glu Asp Pro Ala Ser Arg Glu Leu Val Val Ser Tyr Val Asn Val
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ser Arg Glu Leu Val Val Ser Tyr Val Asn Val Asn Met Gly Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Val Val Ser Tyr Val Asn Val Asn Met Gly Leu Lys Ile Arg Gln
1               5                   10                  15

<210> SEQ ID NO 26
<211> LENGTH: 15
<212> TYPE: PRT
<213> ORGANISM: Artificial Sequence
<220> FEATURE:
```

<223> OTHER INFORMATION: Synthetic

<400> SEQUENCE: 26

Val Asn Val Asn Met Gly Leu Lys Ile Arg Gln Leu Leu Trp Phe
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Met Gly Leu Lys Ile Arg Gln Leu Leu Trp Phe His Ile Ser Cys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Ile Arg Gln Leu Leu Trp Phe His Ile Ser Cys Leu Thr Phe Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Leu Trp Phe His Ile Ser Cys Leu Thr Phe Gly Arg Glu Thr Val
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Ile Ser Cys Leu Thr Phe Gly Arg Glu Thr Val Leu Glu Tyr Leu
1               5                   10                  15

<210> SEQ ID NO 31
<211> LENGTH: 6
<212> TYPE: DNA
<213> ORGANISM: Artificial Sequence
<220> FEATURE:
<223> OTHER INFORMATION: Synthetic

<400> SEQUENCE: 31 ttcgtt                                                          6

<210> SEQ ID NO 32
<211> LENGTH: 9
<212> TYPE: DNA
<213> ORGANISM: Artificial Sequence
<220> FEATURE:
<223> OTHER INFORMATION: Synthetic -continued

```
<400> SEQUENCE: 32 tcgtcgtcg                                                    9
```

1

PHARMACEUTICAL COMPOSITION AND USE THEREOF

CROSS REFERENCE TO RELATED APPLICATIONS

This application is the U.S. national phase of PCT/CN2020/135570, filed on Dec. 11, 2020, which claims priority to Chinese Application No. 201911279536.0, filed on Dec. 13, 2019, each expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 3053-P31USPNP_Seq_List_20221221_ST25_Revised.txt. The text file is 11 KB; was created on Dec. 21, 2022, contains no new matter, and is being submitted via Patent Center.

TECHNICAL FIELD

The present invention belongs to the field of biopharmaceutics. In particular, the present invention relates to a pharmaceutical composition comprising a hepatitis B surface antigen, a hepatitis B core antigen and an immunostimulatory composition, wherein the immunostimulatory composition comprises a saponin and a CpG oligodeoxynucleotide, or consists of an adjuvant comprising a saponin and a CpG oligodeoxynucleotide, and the sequence of the CpG oligodeoxynucleotide has two or more copies of 5'-TTCGTT-3' (SEQ ID NO: 31) motif or 5'-TCGTCGTCG-3' (SEQ ID NO: 32) motif. The present invention also relates to use of the pharmaceutical composition for treating a hepatitis B virus infection and/or a hepatitis B virus mediated disease.

BACKGROUND ART

Hepatitis B virus (HBV) infection is one of serious public health problems worldwide. HBV infection is a significant cause of chronic hepatitis B, cirrhosis and hepatocellular carcinoma (Fatt ovich G. J. Hepatol. 2008; 48: 335-352). Common drugs for the clinical treatment of chronic HBV infection mainly include nucleoside analogues and interferons. Nucleoside analogues cannot completely eliminate cccDNA in hepatocytes, and their long-term use is prone to the emergence of drug-resistant mutants and rebound after drug withdrawal (Kwon H, Lok A S. Nat Rev Gastroenterol Hepatol. 2011; 8: 275-284). Interferons are not suitable for asymptomatic HBV carriers. In chronic HBV patients, the seroconversion incidence of HBeAg is only 33% after half a year of use. Also, the application of interferons is limited by their larger side effects (Tang S X, Yu G L. Lancet 1990; 335 (8684): 302).

At present, the widely used hepatitis B protein vaccines achieve the goal of prevention by inducing humoral immunity and producing protective neutralizing antibodies. Many studies have found that the neutralizing antibodies can only eliminate extracellular viral particles, while elimination of intracellularly infected viruses mainly relies on specific cellular immune responses, Th1-type cytokines such as IFN-$\gamma$ produced by helper T cells, CD4+ T cells, especially virus-specific cytotoxic T lymphocytes (CTL) (ChinR, Lacamini S. Rev Med Viorl. 2003: 13 (4): 255-72). The intensity of cellular immune response directly determines the prognosis of hepatitis B. Therefore, an ideal therapeutic hepatitis B vaccine needs to induce both specific humoral and cellular immunity to break through the immune tolerance of hepatitis B. For example, Chinese patent CN104043120B provides a therapeutic hepatitis B vaccine comprising a hepatitis B surface antigen (HBsAg), a hepatitis B core antigen (HBcAg) and an oligodeoxynucleotide (CpG), which can break through the immune tolerance of hepatitis B and be used for treating viral hepatitis B, especially chronic hepatitis B.

The present inventors have intensively studied the prior art and found that adjuvants play an important role in the therapeutic effect of therapeutic hepatitis B vaccine. The adjuvants, oligodeoxynucleotides (CpGs), are commonly used as immunostimulatory compounds, and their chemical nature is an oligodeoxynucleotide containing cytosine-guanine dinucleotide, which have a similar immune response to the natural pattern recognition receptors for CpG, and can bind to Toll-like receptors on cell membrane, effectively triggering mammalian immune response through TLR9 signaling pathway. Saponin adjuvants are a class of glycosides, the aglycons of which are triterpene or spirostane compounds, and belong to plant-derived adjuvants. Among them, quillaja saponin (QS) is the saponins extracted from quillaja, and QS-21 is the most widely reported adjuvant in QS series. However, QS-21 may induce cell hemolysis and has some systemic and local toxic/side effects. Alving et al.' study (ALVING CR, MATYAS G, BECK Z, et al. Revue Roumaine de Chimie, 2016, 61(8): 631-635) found that ALF liposomes in combination with MPLA and QS-21 as an adjuvant against HIVgp140 protein can effectively increase the antibody titer in serum. Ng et al. (NG H, FERNANDO G J P, DEPELSENAIRE A C I, et al. Scientific Reports, 2016, 6(1): 228-230) used a subcutaneous delivery technique, a nano-patch, to form an adjuvant complex with QS-21. The results showed, compared with traditional intramuscular injection, the nano-patch could significantly reduce the dosages of antigen and QS-21, and induce a higher IgG titer (Ziyi Han, Zhongliang Zeng, Modern Agricultural Science and Technology, 2019 (14): 220-221).

Immunostimulatory compositions comprising a saponin and a CpG oligodeoxynucleotide have been reported in the prior art (WO2001051083A3), wherein the CpG adjuvant involves CpG1826 and CpG7909. However, the effects of CpG adjuvants having different sequences differentiate greatly due to the structural diversity of CpG oligodeoxynucleotides.

Therefore, there is a current need for adjuvants and hepatitis B therapeutics with a stronger immune effect.

Contents of the Invention

In view of the deficiencies in the prior art, the inventors have unexpectedly discovered, after extensive research, an immunostimulatory composition with a stronger immune effect, and a pharmaceutical composition comprising the immunostimulatory composition. The present invention provides a pharmaceutical composition comprising a dual adjuvant, in which the saponin and CpG oligodeoxynucleotide show a synergistic effect with high efficiency, which can mediate a more potent immune response. The invention further provides use of the pharmaceutical composition for treating a hepatitis B virus infection and/or a hepatitis B virus mediated disease.

The objects of the present invention are achieved by the following technical solutions.

In one aspect, the present invention provides a pharmaceutical composition comprising:

i) a hepatitis B surface antigen, an active fragment of the antigen, a variant of the antigen, or a mixture of at least two of them;

ii) a hepatitis B core antigen, an active fragment of the antigen, a variant of the antigen, or a mixture of at least two of them;

iii) an immunostimulatory composition comprising a saponin and a CpG oligodeoxynucleotide, or consisting of an adjuvant comprising a saponin and a CpG oligodeoxynucleotide, wherein the sequence of the CpG oligodeoxynucleotide has two or more copies of 5'-TTCGTT-3' (SEQ ID NO: 31) motif or 5'-TCGTCGTCG-3' (SEQ ID NO: 32) motif.

In the pharmaceutical composition according to the present invention, the sequence of the CpG oligodeoxynucleotide is any one selected from: CpG T1: TCG TTC GTT CGT TCG TTC GTT (SEQ ID NO: 6); CpG T2: TCG TTC GTT CGT TCG TTC GTT CGT T (SEQ ID NO: 7); and CpG T3: TCG TCG TCG TCG TCG TCG TCG (SEQ ID NO: 8).

Preferably, the sequence of the CpG oligodeoxynucleotide is CpG T1: TCG TTC GTT CGT TCG TTC GTT (SEQ ID NO: 6).

In the pharmaceutical composition according to the present invention, the saponin can be one or more selected from the group consisting of quillaja saponin, ginsenoside, platycodin, astragaloside, notoginsenoside, glycyrrhizin, cortex albiziae saponin, ophiopogonin, saikosaponin and *panax japonicus* saponin. Preferably, the saponin is quillaja saponin, ginsenoside, platycodin or astragalin A. More preferably, the quillaja saponin is QS-7, QS-17, QS-18 or QS-21. Further preferably, the quillaja saponin is QS-21. The ginsenoside may be ginsenoside Rgl, ginsenoside Rg3, ginsenoside Rbl or ginsenoside Re. The platycodin may be platycodin D, platycodin D2 or a mixture thereof. The astragaloside may be a monomer such as astragalin A (astragaloside IV), astragaloside I, astragaloside II, and the like, or a mixture of two or more of these saponin monomers. The notoginsenoside may be notoginsenoside R1. The ophiopogonin may be ophiopogonin D or the like. The saikosaponin may be saikosaponin a, saikosaponin d, or a mixture thereof. The cortex albiziae saponin may be cortex albiziae total saponins or the like. The glycyrrhizin may be total glycyrrhizins. The *Panax japonicus* saponin may be *Panax japonicus* total saponins.

In the pharmaceutical composition according to the invention, the adjuvant comprising a saponin is an immunostimulating complex adjuvant (Iscom adjuvant).

In the pharmaceutical composition according to the present invention, the CpG oligodeoxynucleotide may comprise a phosphorothioate linkage. Preferably, the CpG oligodeoxynucleotide is a thio-oligodeoxynucleotide, more preferably a perthio-oligodeoxynucleotide.

In the pharmaceutical composition according to the present invention, the weight ratio of the CpG oligodeoxynucleotide to the saponin is 1~40:0.1~2, preferably 2~40:0.1~2.

Preferably, the weight ratio of the CpG oligodeoxynucleotide to the saponin is 1:0.1, 1:1, 1:2, 2:0.1, 2:1, 40:0.1, 40:1 or 20:1, more preferably 1:1, 2:1, 40:0.1, 40:1 or 20:1, further preferably 2:1.

In the pharmaceutical composition according to the present invention, the hepatitis B surface antigen comprises or consists of the sequence as shown by SEQ ID NO: 1.

In the pharmaceutical composition according to the present invention, the hepatitis B core antigen comprises or consists of the sequence as shown by SEQ ID NO: 2. Preferably, the active fragment of hepatitis B core antigen comprises or consists of consecutive amino acids from position 1 to position X of SEQ ID NO: 2, wherein X may be an integer between 149 and 183, further preferably, X is an integer between 152 and 183.

In the pharmaceutical composition according to the present invention, the weight ratio among Components i), ii) and iii) in the pharmaceutical composition is 4:2:1.1~42, preferably 4:2:2.1~42.

Further preferably, the weight ratio among Components i), ii) and iii) in the pharmaceutical composition is 4:2:1.1, 4:2:2, 4:2:3, 4:2:2.1, 4:2:40.1, 4:2:41 or 4:2:42, preferably 4:2:2, 4:2:3, 4:2:40.1, 4:2:41 or 4:2:42, further preferably 4:2:3.

The pharmaceutical composition according to the invention further comprises:

iv) a pharmaceutically acceptable carrier.

In another aspect, the present invention provides a hepatitis B prophylactic or therapeutic vaccine, comprising the pharmaceutical composition. Preferably, the vaccine is a hepatitis B therapeutic vaccine.

In yet another aspect, the present invention provides use of the pharmaceutical composition in the preparation of a medicament for preventing and/or treating a hepatitis B virus infection and/or a hepatitis B virus mediated disease. Preferably, the hepatitis B virus infection and/or the hepatitis B virus mediated disease is selected from the group consisting of hepatitis B, cirrhosis and liver cancer.

In yet another aspect, the present invention provides use of the pharmaceutical composition in the preparation of a medicament for generating a humoral immune response and/or a cellular immune response against the hepatitis B virus in a subject.

In yet another aspect, the present invention provides use of the pharmaceutical composition in the preparation of a medicament for switching the subtype of hepatitis B core antibody in a subject.

In yet another aspect, the present invention provides use of the pharmaceutical composition in the preparation of a medicament for breaking through the immune tolerance of hepatitis B virus in a subject.

In yet another aspect, the present invention provides a method for preventing and/or treating a hepatitis B virus infection and/or a hepatitis B virus mediated disease comprising administering to a subject in need thereof a prophylactically and/or therapeutically effective amount of the pharmaceutical composition.

Preferably, the hepatitis B virus infection and/or the hepatitis B virus mediated disease is selected from the group consisting of hepatitis B, cirrhosis and liver cancer.

In yet another aspect, the present invention provides a method for generating a humoral immune response and/or a cellular immune response against the hepatitis B virus in a subject, comprising administering to a subject in need thereof an effective amount of the pharmaceutical composition.

In yet another aspect, the present invention provides a method for switching the subtype of hepatitis B core antibody in a subject, comprising administering to a subject in need thereof an effective amount of the pharmaceutical composition.

In yet another aspect, the present invention provides a method for breaking through the immune tolerance of hepatitis B virus in a subject, comprising administering to a subject in need thereof an effective amount of the pharmaceutical composition.

The pharmaceutical composition of the invention comprises two adjuvants, which has unexpected technical effect of mediating a stronger immune response. The immunostimulation effect of CpG T1, CpG T2 or CpG T3 alone is weaker than that of CpG1018, CpG7909 or CpG1826, etc. However, when combined with QS21, the adjuvants exhibit an unexpected synergistic effect, and the immune effects are significantly enhanced. The hepatitis B therapeutic vaccine containing the immunostimulatory composition can break through the immune tolerance of transgenic mice and produce high titers of anti-HBsAg antibodies, anti-HBcAg antibodies and neutralizing antibodies. Various test results show that this vaccine could significantly eliminate the hepatitis B virus in transgenic mice through multiple immunizations. At the end of the immunization process, the HBsAb level was close to saturation, which could maintain a long-term stable immune effect, and the average decrease rate of HBsAg was maintained at about 92%. Meanwhile, the Hepatitis B vaccine containing the immunostimulator could induce stronger levels of HBsAg- and HBcAg-specific IFN-$\gamma$, and the immune effect is significantly better than that of either adjuvant alone or the combinations of other CPG adjuvants and QS21.

BRIEF DESCRIPTION OF THE DRAWINGS

The embodiments of the present invention will be described below in detail in conjunction with the accompanying drawings, in which.

6

Figure 11:
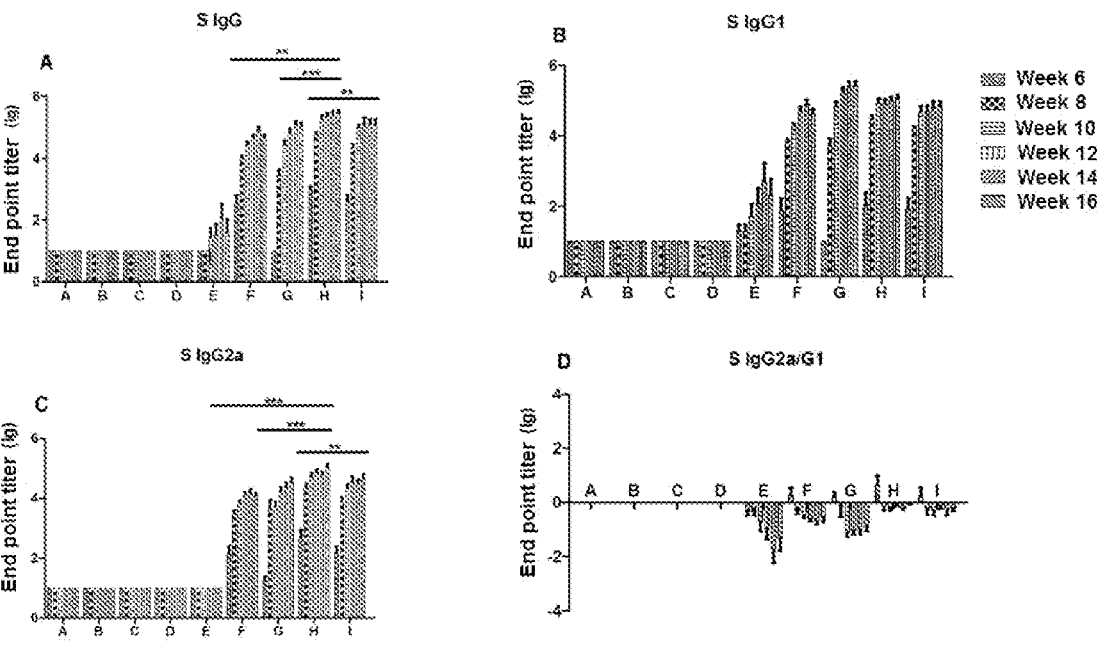

FIG. 11 shows the effects of the hepatitis B vaccines containing the immunostimulatory composition of the present invention on the levels of HBsAg antigen-specific IgG antibody and subtypes thereof in the mouse serum; wherein Panel A: HBsAb IgG levels in the mouse serum for all the groups; Panel B: HBsAb IgG1 levels in the mouse serum for all the groups; Panel C: HBsAb IgG2a levels in the mouse serum for all the groups; Panel D: the ratios of HBsAb IgG2a to IgG1 in the mouse serum for all the groups.

Figure 12:
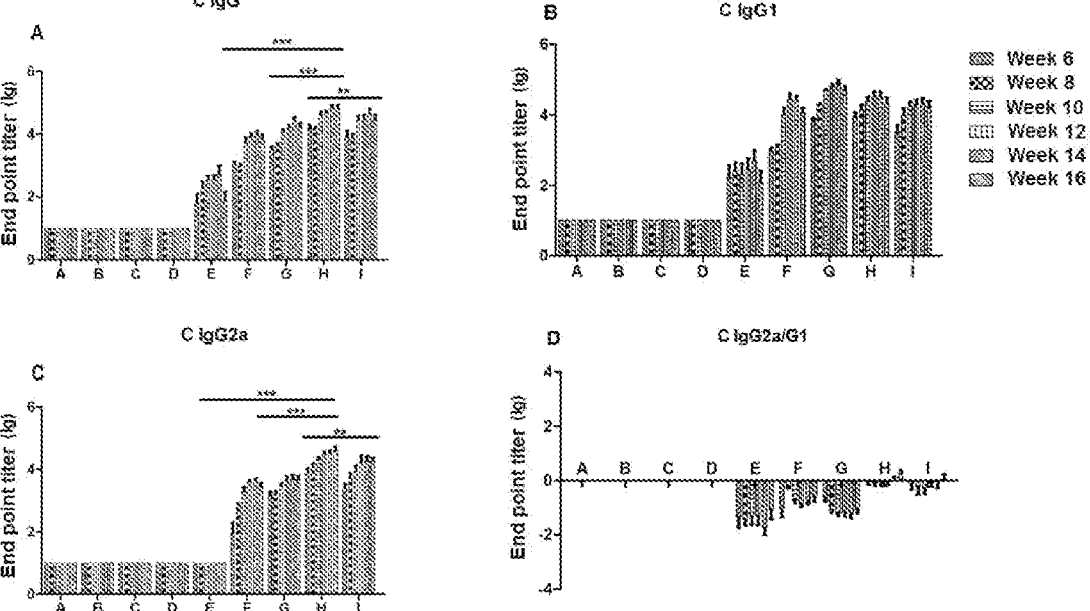

FIG. 12 shows the effects of the hepatitis B vaccines containing the immunostimulatory composition of the present invention on the levels of HBcAg antigen-specific IgG antibody and subtypes thereof in the mouse serum; wherein Panel A: HBcAb IgG levels in the mouse serum for all the groups; Panel B: HBcAb IgG1 levels in the mouse serum for all the groups; Panel C: HBcAb IgG2a levels in the mouse serum for all the groups; Panel D: the ratios of HBcAb IgG2a to IgG1 in the mouse serum for all the groups.

Figures 13, 14:
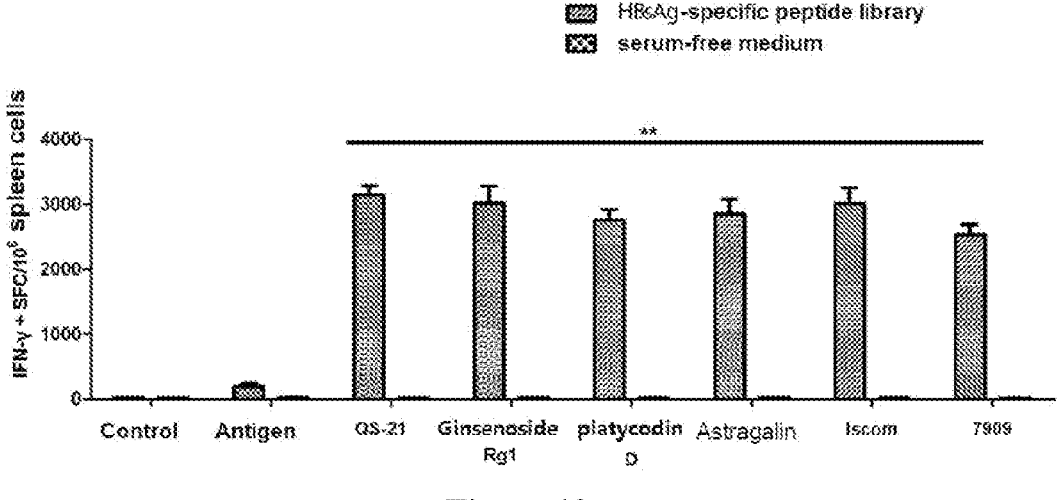

FIG. 13 shows the effects of the immunostimulatory compositions containing different saponins on the secretion level of HBsAg antigen-specific IFN-$\gamma$.

FIG. 14 shows the effects of the immunostimulatory compositions containing different saponins on the secretion level of HBcAg antigen-specific IFN-$\gamma$.

DEFINITIONS

Unless defined otherwise, all the scientific and technical terms used herein have the same meaning as understood by one of ordinary skill in the art. With regard to the definitions and terms in the art, one of skill can refer specifically to Current Protocols in Molecular Biology (Ausubel). The abbreviations for amino acid residues are standard 3-letter and/or 1-letter codes used in the art to refer to one of 20 common L-amino acids.

Although the present invention shows the numerical ranges and approximations of parameters in broad scopes, the numerical values shown in the specific examples are reported as precisely as possible. All the numerical values, however, inherently contain a certain error necessarily resulting from the standard deviations found in their respective measurements. Additionally, all the ranges disclosed herein are to be understood to encompass any and all the subranges subsumed therein. For example, a stated range of "1.1 to 42" should be considered to include any and all the subranges between (and inclusive of) the minimum value of 1.1 and the maximum value of 42, that is, all the subranges beginning with a minimum value of 1.1 or more, e.g. 1.1 to 6.1, and ending with a maximum value of 42 or less, e.g. 5.5 to 42. Further, any reference referred to as "incorporated herein" is understood to be incorporated in its entirety.

It is further noted that, as used in this specification, the singular forms include the plural forms of the referents to which they refer, unless expressly and unequivocally limited to one referent. The term "or" may be used interchangeably with the term "and/or", unless the context clearly dictates otherwise.

As used herein, the terms "pharmaceutical composition", "combination drug", and "drug combination" may be used interchangeably and refer to a combination of at least one drug, and optionally a pharmaceutically acceptable excipient or auxiliary material, which are combined together to achieve a certain particular purpose. In certain embodiments, the pharmaceutical composition includes temporally and/or spatially separated components, so long as they are capable of cooperating to achieve the objects of the present invention. For example, the ingredients (e.g. HBsAg, HBcAg, QS-21, and CpG oligodeoxynucleotide) contained in the pharmaceutical composition may be administered to a subject as a whole or separately. When the ingredients contained in the pharmaceutical composition are administered separately to a subject, the ingredients may be administered to the subject simultaneously or sequentially.

As used herein, the term "CpG oligodeoxynucleotide" or "CpG-ODN" refers to a short single-chain synthetic DNA molecule containing one or more "CpG" unit(s), wherein C represents cytosine, G represents guanine and p represents a phosphodiester bond. In particular, the CpG oligodeoxynucleotide is non-methylated. In some embodiments, the CpG-ODN comprises a phosphorothioate linkage or a phosphorothioate backbone. That is to say, in some embodiments, the CpG-ODN is a phosphorothioate oligodeoxynucleotide (i.e. a thio-oligodeoxynucleotide). Preferably, all the internucleotide linkages in the CpG-ODN are phosphorothioate linkages, that is, the CpG-ODN is a perthiooligodeoxynucleotide. In other embodiments, the CpG-ODN comprises two or more copies of 5'-TTCGTT-3' (SEQ ID NO: 31) motif or 5'-TCGTCGTCG-3' (SEQ ID NO: 32) motif. In particular, the CpG-ODN has a sequence selected from: TCG TTC GTT CGT TCG TTC GTT (SEQ ID NO: 6), TCG TTC GTT CGT TCG TTC GTT CGT T (SEQ ID NO: 7), or TCG TCG TCG TCG TCG TCG TCG (SEQ ID NO: 8), preferably TCG TTC GTT CGT TCG TTC GTT (SEQ ID NO: 6).

As used herein, "ginsenoside, platycodin, astragaloside, notoginsenoside, glycyrrhizin, cortex albiziae saponin, ophiopogonin, saikosaponin or *Panax japonicus* saponin" refer to an active ingredient presented in the corresponding plant. For example, ginsenoside is a kind of sterol compounds, which mainly exist in the medicinal materials of genus *Panax* and are active ingredients in *ginseng*. In some embodiments, the ginsenoside is preferably a monomer such as ginsenoside Rgl, ginsenoside Rg3, ginsenoside Rbl, ginsenoside Re, or a mixture of two or more of these saponin monomers. The platycodin is preferably platycodin D, platycodin D2 or a mixture thereof. The astragaloside is preferably a monomer such as astragalin A (astragaloside IV), astragaloside I, astragaloside II, and the like, or a mixture of two or more of these saponin monomers. The notoginsenoside is preferably notoginsenoside R1, or the like. The ophiopogonin is preferably ophiopogonin D, or the like. The saikosaponin is preferably saikosaponin a, saikosaponin d, or a mixture thereof. The cortex albiziae saponin is preferably cortex albiziae total saponins or the like. The glycyrrhizin is preferably total glycyrrhizins or the like. The *Panax japonicus* saponin is preferably *Panax japonicus* total saponins or the like.

As used herein, "Iscom adjuvant" is an immunostimulatory complex adjuvant, specifically ISCOM MATRIX that does not comprise an antigen, which is an adjuvant composed of a phospholipid, a saponin, and cholesterol with a cage-like structure.

As used herein, "a therapeutically effective amount" or "an effective amount" refers to a dosage sufficient to show its benefit to the subject to which it is administered. The actual amount administered, as well as the rate and time course of administration, would depend on the own conditions and severity of the subject being treated. A prescription of treatment (e.g. determination of dosage, etc.) is ultimately the responsibility of, and determined by, general practitioners and other physicians, often taking into account the disease to be treated, the conditions of the individual patient, the site of delivery, the method of administration, and other factors known to physicians.

As used herein, the term "mammal" refers to a human, and may also be other animals, such as wild animals (e.g. herons, storks, cranes, etc.), domestic animals (e.g. ducks, geese, etc.) or laboratory animals (e.g. chimpanzees, monkeys, rats, mice, rabbits, guinea pigs, woodchucks, ground squirrels, etc.).

In other embodiments, the composition of the present invention may further comprise an additional additive, such as a pharmaceutically acceptable carrier or additive, particularly when presented as a pharmaceutical formulation form.

The preferred pharmaceutical carrier is especially water, buffered aqueous solutions, preferably isotonic saline solutions such as PBS (phosphate buffer), glucose, mannitol, dextrose, lactose, starch, magnesium stearate, cellulose, magnesium carbonate, 0.3% glycerol, hyaluronic acid, ethanol or polyalkylene glycols such as polypropylene glycol, triglycerides, etc. The types of pharmaceutical carrier used depend inter alia on whether the composition according to the present invention is formulated for oral, nasal, intradermal, subcutaneous, intramuscular or intravenous administration. The composition according to the present invention may comprise a wetting agent, an emulsifying agent or buffer substance as an additive.

The pharmaceutical composition, vaccine or pharmaceutical formulation according to the present invention may be administered by any suitable route, for example, oral, nasal, intradermal, subcutaneous, intramuscular or intravenous administration.

The present invention is further illustrated by the following description of specific embodiments in conjunction with the accompanying drawings, which are not to be construed as limitation of the present invention, and various modifications or improvements can be made by those skilled in the art in light of the basic concepts of the present invention, which are all within the scope of the present invention, as long as they do not deviate from the basic concepts of the present invention.

BEST MODES FOR CARRYING OUT THE INVENTION

The present invention is illustrated below with reference to the specific examples. Those skilled in the art will appreciate that these examples are merely illustrative of the present invention and not intended to limit the scope of the present invention in any way.

The experimental methods in the following examples are conventional, unless otherwise specified. The raw materials, reagent materials and the like used in the following examples are commercially available products, unless otherwise specified.

Example 1 Preparation of Screening Experiment on Immunostimulatory Compositions 1. HBsAg stock solution: the amino acid sequence of the HBsAg protein is shown by SEQ ID NO: 1.

The HBsAg protein was prepared from recombinant yeast cells of the HBsAg gene, and the types of yeast cells include *Hansenula, Saccharomyces cerevisiae* and *Pichia*, preferably *Hansenula*. For the specific preparation steps, reference was made to Chinese patent application CN108330145A. The recombinant *Hansenula* cells of the HBsAg gene were cultured by fermentation and the mycelia were harvested. The mycelia were subjected to disruption treatment and purified by the steps of silica gel adsorption, column chromatography and TFF, etc.

2. HBcAg stock solution: the amino acid sequence of the HBcAg protein is shown by SEQ ID NO: 2.

The HBcAg protein was prepared from recombinant yeast cells of the HBcAg gene, and the types of yeast cells include *Hansenula, Saccharomyces cerevisiae* and *Pichia*, preferably *Hansenula*. For the specific preparation steps, reference was made to Chinese patent application CN108047316A. The recombinant *Hansenula* cells of the HBcAg gene were cultured by fermentation and the mycelia were harvested. The mycelia were subjected to disruption treatment and purified by the steps of ammonium sulfate treatment, column chromatography and TFF, etc. to prepare the HBcAg stock solution.

3. QS-21 was purchased from BRENNTAG, CAS. NO. A010-023.

4. Preparation method of CPG oligodeoxynucleotide raw materials:

Oligodeoxynucleotides are synthetically prepared fragments of oligodeoxynucleotide sequence containing one or more CpG motifs. The CPG sequences used in this example are shown in Table 1:

hydroxyl, condense and remove the tetrazole, upon which the oligonucleotide chain is extended forward by one base; 4) Oxidation: during the condensation reaction, the nucleotide monomer is connected to the oligonucleotide connected to CpG via a phosphite bond, while the phosphite bond is unstable and prone to be hydrolyzed by an acid or a base, upon which the phosphoramidite is oxidized into a phosphotriester with a sulphur-phosphorus double bond using a thio-substitution reagent, thereby obtaining a stable oligonucleotide; and 5) Blocking: in order to prevent the unreacted 5' hydroxyl connected to CpG from being extended in the subsequent circular reaction after the condensation reaction, this terminal hydroxyl is often blocked by acetylation. After the above five steps, one deoxynucleotide is connected to the nucleotide of CpG. The above deprotection, activation, connection, oxidation and blocking processes are repeated to obtain a crude DNA fragment. Finally, it is

TABLE 1

|  | | Specific sequences of CPG oligodeoxynucleotide |
|---|---|---|
| Typing of CPG Oligodeoxynucleotide | CPG Oligodeoxynucleotide | Sequence |
| Type B | CpG 1018 | TGACTGTGAACGTTCGAGATGA (SEQ ID NO: 3) |
|  | CpG 7909 | TCGTCGTTTTGTCGTTTTGTCGTT (SEQ ID NO: 4) |
|  | CpG 1826 | TCCATGACGTTCCTGACGTT (SEQ ID NO: 5) |
|  | CpG T1 | TCGTTCGTTCGTTCGTTCGTT (SEQ ID NO: 6) |
|  | CpG T2 | TCG TTC GTT CGT TCG TTC GTT CGT T (SEQ ID NO: 7) |
|  | CpG T3 | TCG TCG TCG TCG TCG TCG TCG (SEQ ID NO: 8) |
|  | CpG 684 | TCGACGTTCGTCGTTCGTCGTTC (SEQ ID NO: 9) |
|  | CpG 1668 | TCC ATG ACG TTC CTG ATGCT (SEQ ID NO: 10) |
|  | CpG D2 | TGTCGTCGTCGTTTGTCGTTTGTCGTT (SEQ ID NO: 11) |
| Type A | CpG 2216 | GGGGGACGATCGTCGGGGGG (SEQ ID NO: 12) |
|  | ODN 2336 | GGGGACGACGTCGTGGGGGGG (SEQ ID NO: 13) |
| Type C | ODN 2395 | TCGTCGTTTCGCGCGCGCCG (SEQ ID NO: 14) |
|  | ODN M362 | TCGTCGTTCGTTCGTCGAACGACGTTTGAT (SEQ ID NO: 15) |

The specific preparation method: a conventional solid phase phosphoramidite-phosphotriester chemical synthesis method was used for the preparation, starting from the 3' end, i.e., 1) Deprotection: first removing the protecting group DMT (dimethoxytrityl) of the nucleotide connected to CpG with trichloroacetic acid to obtain free 5' hydroxyl for the next step of condensation reaction; 2) Activation: mixing a phosphoramidite-protected nucleotide monomer and a tetrazole activator into a synthesis column to form a phosphoramidite tetrazole active intermediate, which undergoes a condensation reaction with a deprotected nucleotide on CpG; 3) Connection: when the phosphoramidite tetrazole reactive intermediate encounters the deprotected nucleotide on CpG, it will undergo an affinity reaction with its 5' subjected to post-synthesis treatments, such as cleavage, deprotection, purification and quantification, etc.

5. The HbsAg stock solution and the HbcAg stock solution were diluted to 200 μg/ml and 100 μg/ml respectively, using a PBS solution (purchased from Hyclone). All the CPG raw materials were separately dissolved and diluted to 100 μg/ml using the PBS solution, for the next step.

Example 2 Screening Experiment of CPG Oligodeoxynucleotides

1. Experimental animals: C57BL/6(N) mice, male, 4 weeks old, 135 mice, Shanghai Lingchang Laboratory Animal Technology Co. Ltd.

2. Experimental grouping: see Table 2. The dosage for each injection was 100 μL/mouse, and Group A was the negative control (the PBS solution, 100 μL/mouse).

TABLE 2

Grouping of experimental animals

| | | Component (μg/mouse) | | | | | | | | | | | | | | | |
|---|---|---|---|---|---|---|---|---|---|---|---|---|---|---|---|---|---|
| Group | Number (animals) | HBs Ag | HBc Ag | CpG T1 | CpG T2 | CpG T3 | CpG 1018 | CpG 7909 | CpG 1826 | CpG 684 | CpG 1668 | CPG D2 | CpG 2216 | ODN 2336 | ODN 2395 | ODN M362 |
| Control | 9 | | | | | | | | | | | | | | | |
| Antigen | 9 | 20 | 10 | | | | | | | | | | | | | |
| T1 | 9 | 20 | 10 | 10 | | | | | | | | | | | | |
| T2 | 9 | 20 | 10 | | 10 | | | | | | | | | | | |
| T3 | 9 | 20 | 10 | | | 10 | | | | | | | | | | |
| 1018 | 9 | 20 | 10 | | | | 10 | | | | | | | | | |
| 7909 | 9 | 20 | 10 | | | | | 10 | | | | | | | | |
| 1826 | 9 | 20 | 10 | | | | | | 10 | | | | | | | |
| 684 | 9 | 20 | 10 | | | | | | | 10 | | | | | | |
| 1668 | 9 | 20 | 10 | | | | | | | | 10 | | | | | |
| D2 | 9 | 20 | 10 | | | | | | | | | 10 | | | | |
| 2216 | 9 | 20 | 10 | | | | | | | | | | 10 | | | |
| 2336 | 9 | 20 | 10 | | | | | | | | | | | 10 | | |
| 2395 | 9 | 20 | 10 | | | | | | | | | | | | 10 | |
| M362 | 9 | 20 | 10 | | | | | | | | | | | | | 10 |

3. Experimental steps: on Day 7 after the immunization of mice, the spleen lymphocytes were prepared according to a conventional method, and the details were as follows: the spleens were taken aseptically by being cut with sterile forceps and scissors, and placed in a 70 μm cell strainer, which was placed in a plate containing 2 ml of pre-chilled 2% FBS (purchased from GIBCO)-PBS; the spleens were ground using a grinding rod, and the spleen cells entered the plate through the meshes to obtain a cell suspension, and then the suspension was filtered by a 40 μm cell strainer (purchased from BD) and put into a 50 ml sterile centrifuge tube by using a Pasteur pipet; it was centrifuged at 500×g at 4° C. for min; the supernatant was discarded, and then 2 ml of 1× erythrocyte disruption agent (purchased from BD) was added to re-suspend the cells, and the resultant was allowed to stand for 5 min at 4° C., protected from light to disrupt the red blood cells; 10 ml of 2% FBS-PBS was added to terminate the erythrocyte disruption reaction; the resultant was centrifuged at 500×g at 4° C. for 5 min, the supernatant was discarded, and then 5 ml of 2% FBS-PBS was added to re-suspend the cells for later use. The spleen cells were stimulated with the stimulators, HBsAg-specific peptide library PS4 and HBcAg-specific peptide library PCP, respectively. An ELISPOT kit (BD) was used to detect the secretion levels of HBsAg and HBcAg antigen-specific IFN-γ according to the kit instructions. The spot number measured by the ELISPOT kit were read using ImmunoSPOT Series 3 Elispot analyzer (refer to Example 7 of Chinese patent CN104043120B for the specific operation steps).

The sequences of HBsAg-specific peptide library refer to Example 7 of Chinese patent CN104043120B, and the sequences of HBcAg-specific peptide library are shown by SEQ ID NO: 16-30.

Figure 1:
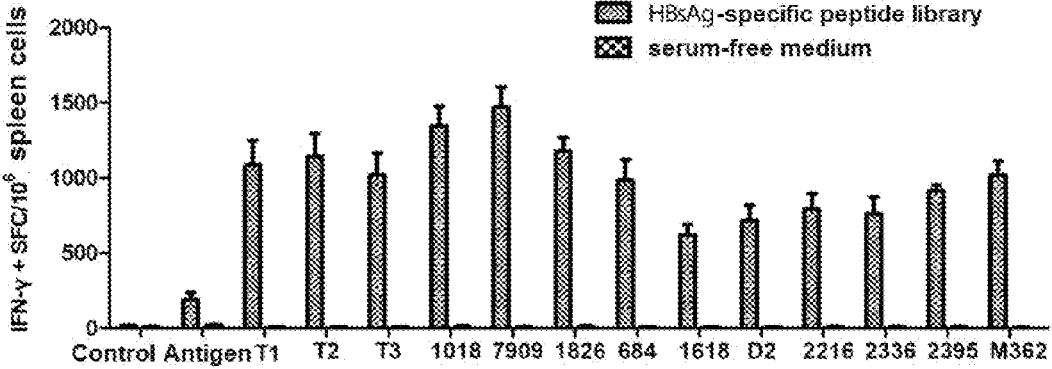
FIG. 1 shows the effects of different CPG oligodeoxynucleotides on the secretion level of HBsAg antigen-specific IFN-$\gamma$.
Figure 2:
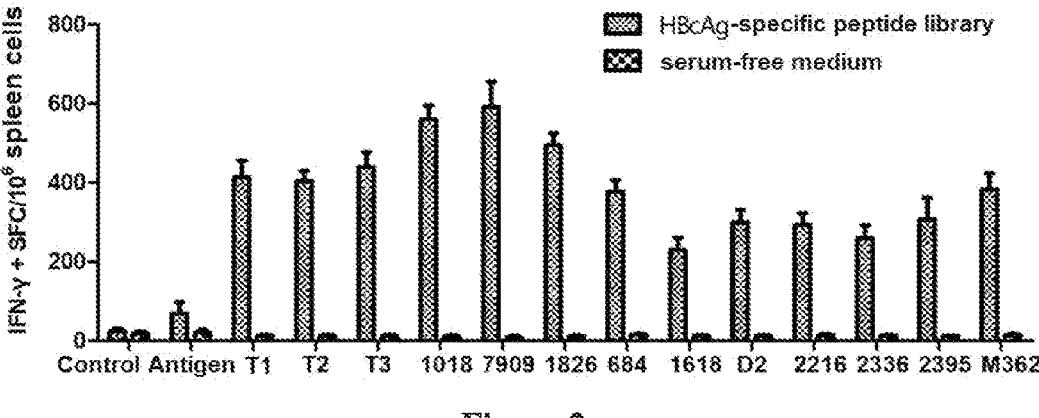
FIG. 2 shows the effects of different CPG oligodeoxynucleotides on the secretion level of HBcAg antigen-specific IFN-$\gamma$.

4. Experimental results: the results of ELISPOT spot are shown in FIG. 1 and FIG. 2. The results show that the CpG adjuvants of type B with different sequences had different immune effects. Among them, CpG T1-T3, CpG 1018, CpG 7909, CpG 1826 and CpG 684 as a whole were superior to the CpG adjuvants of type A and the CpG adjuvants of type C, while CpG 1618 and CPG D2 had poorer immune effects, and the induced production levels of HBsAg- and HBcAg-specific IFN-γ were all lower than those induced by the CpG adjuvants of type A and the CpG adjuvants of type C.

Example 3 Screening Experiment of Immunostimulatory Compositions

1. Experimental animals: C57BL/6(N) mice, male, 4 weeks old, 81 mice, Shanghai Lingchang Laboratory Animal Technology Co. Ltd.

2. Experimental grouping: see Table 3. The dosage for each injection was 100 μL/mouse, and Group A was the negative control (the PBS solution, 100 μL/mouse).

TABLE 3

Grouping of experimental animals

| | | Component (μg/mouse) | | | | | | | | | |
|---|---|---|---|---|---|---|---|---|---|---|---|
| Group | Number (animals) | HBsAg | HBcAg | CpG T1 | CpG T2 | CpG T3 | CpG 1018 | CpG 7909 | CpG 1826 | CpG 684 | QS21 |
| Control | 9 | | | | | | | | | | |
| Antigen | 9 | 20 | 10 | | | | | | | | |
| T1 | 9 | 20 | 10 | 10 | | | | | | | 5 |
| T2 | 9 | 20 | 10 | | 10 | | | | | | 5 |
| T3 | 9 | 20 | 10 | | | 10 | | | | | 5 |
| 1018 | 9 | 20 | 10 | | | | 10 | | | | 5 |
| 7909 | 9 | 20 | 10 | | | | | 10 | | | 5 |
| 1826 | 9 | 20 | 10 | | | | | | 10 | | 5 |
| 684 | 9 | 20 | 10 | | | | | | | 10 | 5 |

3. Experimental steps: following Example 2.

Figure 3:
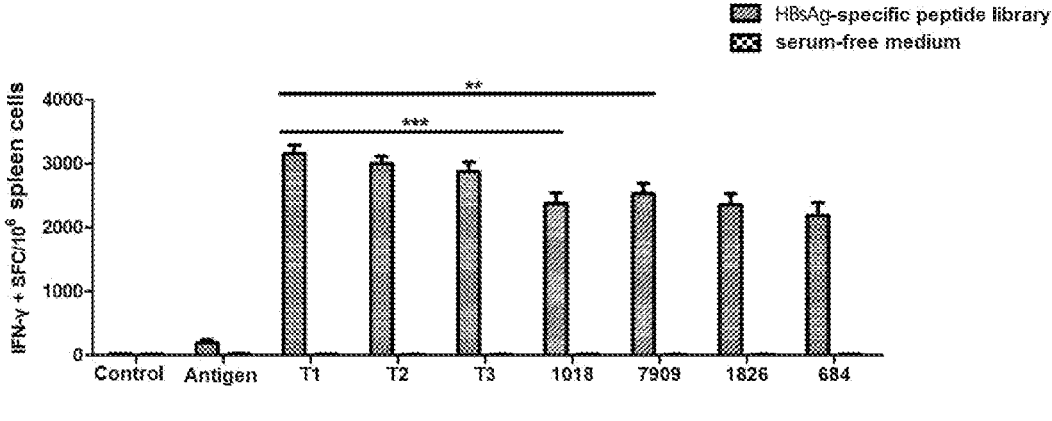
FIG. 3 shows the effects of different immunostimulatory compositions according to the present invention on the secretion level of HBsAg antigen-specific IFN-$\gamma$.
Figure 4:
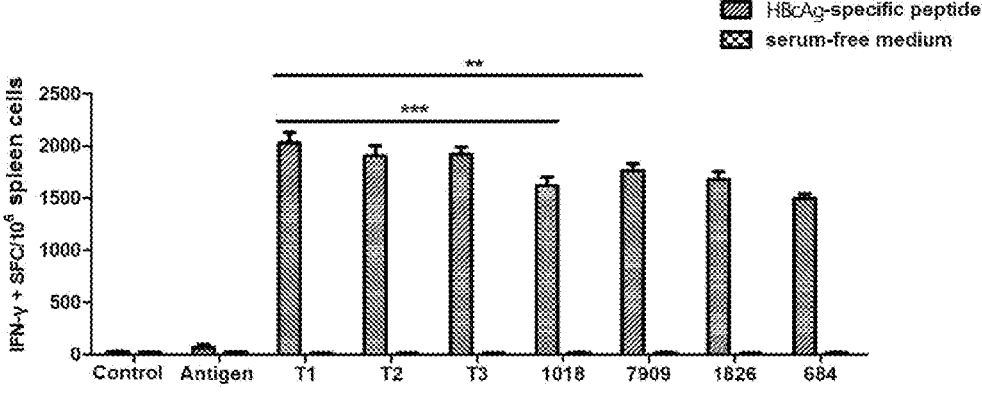
FIG. 4 shows the effects of different immunostimulatory compositions according to the present invention on the secretion level of HBcAg antigen-specific IFN-$\gamma$.

4. Experimental results: the results of ELISPOT spot are shown in FIG. 3 and FIG. 4. The results show that use of CpG T1-T3 in combination with QS21 resulted in a high-efficiency synergistic effect, and the induced production levels of HBsAg- and HBcAg-specific IFN-γ were significantly higher than those induced by other CpG adjuvants, such as CpG 1018, CpG 7909, etc., with unexpected immune effect.

Example 4 Effects of Different Amounts of Adjuvant on Immune Effect of Pharmaceutical Composition 1. Experimental animals: C57BL/6(N) mice, male, 4 weeks old, 60 mice, Shanghai Lingchang Laboratory Animal Technology Co. Ltd.

2. Reagents and materials:

1) The HBsAg protein, HBcAg protein and CpG T1 were obtained from Example 1.

2) QS-21 (CAS. NO. A010-023, purchased from BRENNTAG).

3) The HBsAg stock solution and HBcAg stock solution were diluted to 200 μg/ml and 100 μg/ml respectively, using a PBS solution (purchased from Hyclone); QS21 was diluted to 5 μg/ml, 50 μg/ml and 100 μg/ml respectively; CpG T1 was dissolved and diluted to 50 μg/ml, 100 μg/ml and 2 mg/ml respectively, using the PBS solution; and CPG 7909 was dissolved and diluted to 100 μg/ml using the PBS solution, for the next step.

3. Experimental grouping: see Table 4. The dosage for each injection was 100 μL/mouse, and Group A was the negative control (the PBS solution, 100 μL/mouse).

4. Experimental steps: following Example 2.

Figure 5:
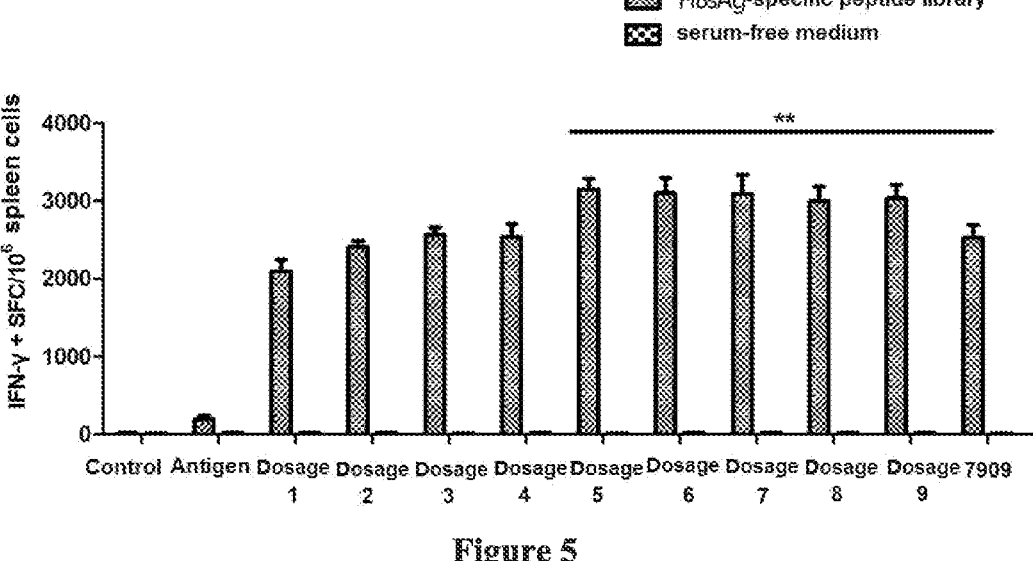
FIG. 5 shows the effects of varying dosages of the immunostimulatory composition according to the present invention on the secretion level of HBsAg antigen-specific IFN-$\gamma$.
Figure 6:
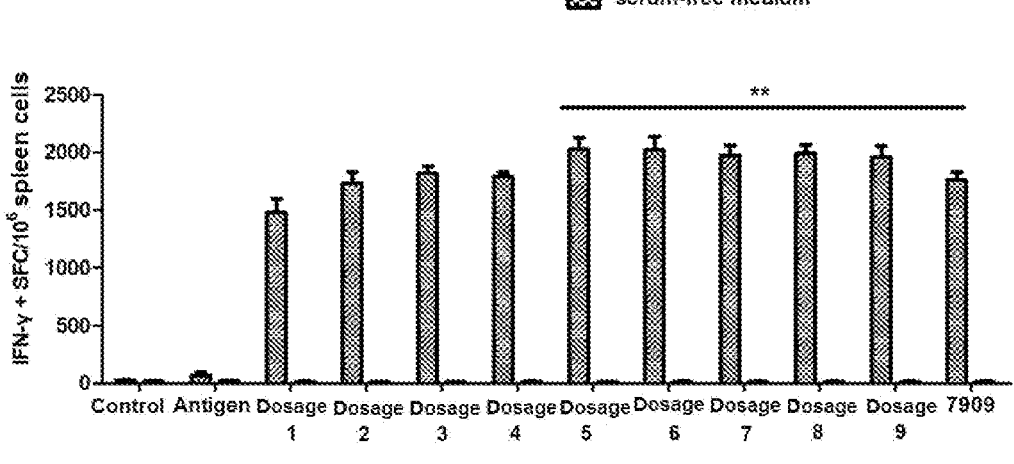
FIG. 6 shows the effects of varying dosages of the immunostimulatory composition according to the present invention on the secretion level of HBcAg antigen-specific IFN-$\gamma$.

5. Experimental results: the results of ELISPOT spot are shown in FIG. 5 and FIG. 6. The results show that the dosage changes of CpG T1 and QS21 had significant effects on the vaccine composition, and the immunostimulatory compositions having a dosage higher than Dosage 5 induced the production levels of HBsAg- and HBcAg-specific IFN-γ which were significantly higher than that of the CPG 7909 group. However, due to the species difference, a further increase of adjuvant dosage did not induce a significant increase of the effect, presumably because the mice could not accurately reflect the immune intensity of adjuvant.

Dosages 1, 2 and 4 were equivalent to CPG 7909 group in terms of immunostimulatory effect, but the adjuvant dosages used were lower than that of the equivalent CPG 7909 group, thus they also had a certain advantage.

TABLE 4

Grouping of experimental animals

| Group | Number (animals) | HBsAg | HBcAg | CpG T1 | QS21 | CPG7909 |
|---|---|---|---|---|---|---|
| | | | | Component (μg/mouse) | | |
| Control | 5 | | | | | |
| Antigen | 5 | 20 | 10 | | | |
| Dosage 1 | 5 | 20 | 10 | 5 | 0.5 | |
| Dosage 2 | 5 | 20 | 10 | 5 | 5 | |
| Dosage 3 | 5 | 20 | 10 | 5 | 10 | |
| Dosage 4 | 5 | 20 | 10 | 10 | 0.5 | |
| Dosage 5 | 5 | 20 | 10 | 10 | 5 | |
| Dosage 6 | 5 | 20 | 10 | 10 | 10 | |
| Dosage 7 | 5 | 20 | 10 | 200 | 0.5 | |
| Dosage 8 | 5 | 20 | 10 | 200 | 5 | |

TABLE 4-continued

Grouping of experimental animals

| Group | Number (animals) | HBsAg | HBcAg | CpG T1 | QS21 | CPG7909 |
|---|---|---|---|---|---|---|
| | | | | Component (μg/mouse) | | |
| Dosage 9 | 5 | 20 | 10 | 200 | 10 | |
| CPG7909 | 5 | 20 | 10 | | 5 | 10 |

Example 5 Experimental Group Setting and Immunization Process for Hepatitis B Vaccines 1. Experimental animals and model establishment: C57BL/6(N) mice, male, 4 weeks old, 81 mice, Shanghai Lingchang Laboratory Animal Technology Co. Ltd.; rAAV 8-HBV adenovirus, purchased from Beijing FivePlus Molecular Medicine Institute Co. Ltd. A C57BL/6(N) mouse model infected persistently with rAAV 8-HBV was established by intravenously injecting rAAV 8-HBV adenovirus into the upper tail vein of C57BL/6 (N) mice.

2. Reagents and materials:

1) HBsAg protein: obtained from Example 1.

2) HBcAg protein: obtained from Example 1.

3) The HBsAg stock solution, HBcAg stock solution and QS-21 were diluted to 200 μg/ml, 100 μg/ml and 50 μg/ml respectively, using a PBS solution (purchased from Hyclone), and CpG was dissolved and diluted to 100 μg/ml using the PBS solution, for the next step.

3. Experimental grouping: see Table 5. The dosage for each injection was 100 μL/mouse, and Group A was the negative control and injected with the PBS solution at 100 μL/mouse).

TABLE 5

Grouping of experimental animals and injection amounts for each group

| Group | Number (animals) | HBsAg | HBcAg | CpG T1 | CpG 7909 | QS-21 |
|---|---|---|---|---|---|---|
| | | | | Component (μg/mouse) | | |
| A | 9 | | | | | |
| B | 9 | | | 10 | | |
| C | 9 | | | | | 5 |
| D | 9 | | | 10 | | 5 |
| E | 9 | 20 | 10 | | | |
| F | 9 | 20 | 10 | 10 | | |
| G | 9 | 20 | 10 | | | 5 |
| H | 9 | 20 | 10 | 10 | | 5 |
| I | 9 | 20 | 10 | | 10 | 5 |

4. Animal immunization: all the groups were administrated by intramuscular injection once every 2 weeks and the inoculation site was at the right rear thigh, with a total of 6 administrations at 4th, 6th, 8th, 10th, 12th and 14th week respectively, after the tail vein intravenous injection of rAAV 8-HBV virus. The blood was collected once every 2 weeks after the start of administration, i.e., at 4th, 6th, 8th, 10th, 12th, 14th, 16th, 18th, 20th and 22th week, respectively. All the mice were sacrificed at 22th week.

Example 6 Effects of Hepatitis B Vaccines on HBsAg Level in Serum

1. Detection steps for serum HBsAg: Nanjing Drum Tower Hospital was entrusted for detection.

Using a two-step immunoassay, the binding between the sample to be detected and the paramagnetic particles coated with the hepatitis B surface antibody was firstly detected; after washing, an acridinium ester-labeled hepatitis B surface antibody conjugate was added; after washing again, a pre-excitation solution and an excitation solution were added to the reaction mixture, and the relative luminescence units (RLU) of the sample to be detected was determined; there was a positive correlation between the content of HBsAg in the sample and RLU, and the concentration of HBsAg in the mouse serum sample was determined via a generated ARCHTITECT HBsAg standard curve; finally, the concentration of HBsAg in the mouse serum sample was 50 to 200 times of the determined value.

Figure 7:
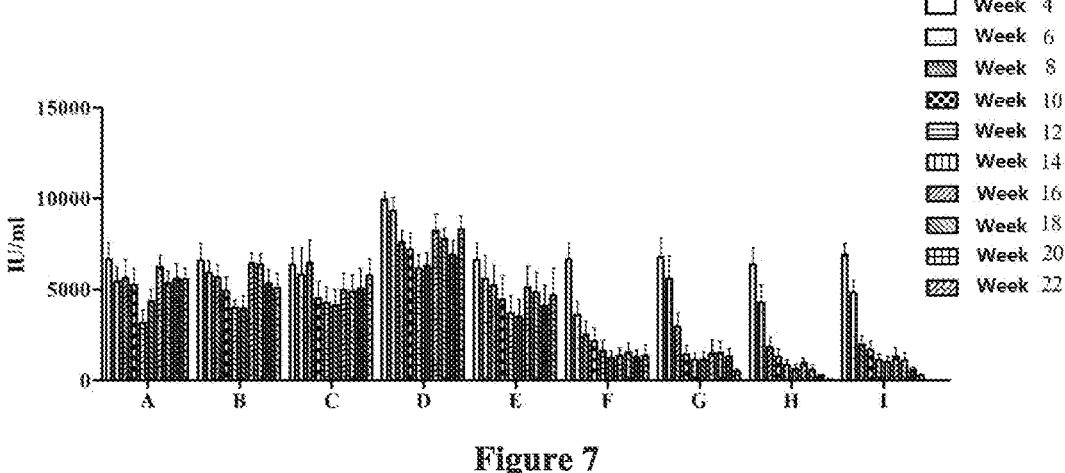
FIG. 7 shows the effects of the hepatitis B vaccines containing the immunostimulatory composition of the present invention on the level of HBsAg in serum.

2. Analysis of results (FIG. 7): Group H vaccine containing the immunostimulator according to the present invention showed a significant downtrend in the corresponding HBsAg level, and maintained a stable long-lasting immune effect after the end of the immunization process (from Week 14), with a significant advantage compared to the CpG group alone (Group F) and the QS-21 group alone (Group G). The HBsAg level in Group H decreased from >6350 IU/ml at the onset to about 50 IU/ml. In this group, the HBsAg level decreased by more than 30% after the second immunization (Week 6) and decreased by more than 70% after the third immunization (Week 8), and the average decrease rate was maintained at about 92% after the end of immunization at Week 14. A superior immune effect was found. Compared with the dual adjuvant control (Group I), Group H still maintained a stable immune effect after the end of immunization at Week 14, and the immune level was significantly better than that of Group I.

Example 7 Evaluation of Humoral Immune Effects of Hepatitis B Vaccines

1. Detection steps for serum HBsAb: Nanjing Drum Tower Hospital was entrusted for detection.

Using a two-step immunoassay, the sample to be detected was first mixed with the paramagnetic particles coated with the recombinant HBsAg (rHBsAg); after washing, an acridinium ester-labeled rHBsAg conjugate was added; after washing again, a pre-excitation solution and an excitation solution were added to the reaction mixture, and the relative luminescence unit (RLU) of the sample to be detected was determined; there was a positive correlation between the content of HBsAb in the sample and RLU, and the concentration of HBsAg in the mouse serum sample was determined via a generated ARCHTITECT HBsAb standard curve; finally, the concentration of HBsAb in the mouse serum sample was 50 to 200 times of the determined value.

Figure 8:
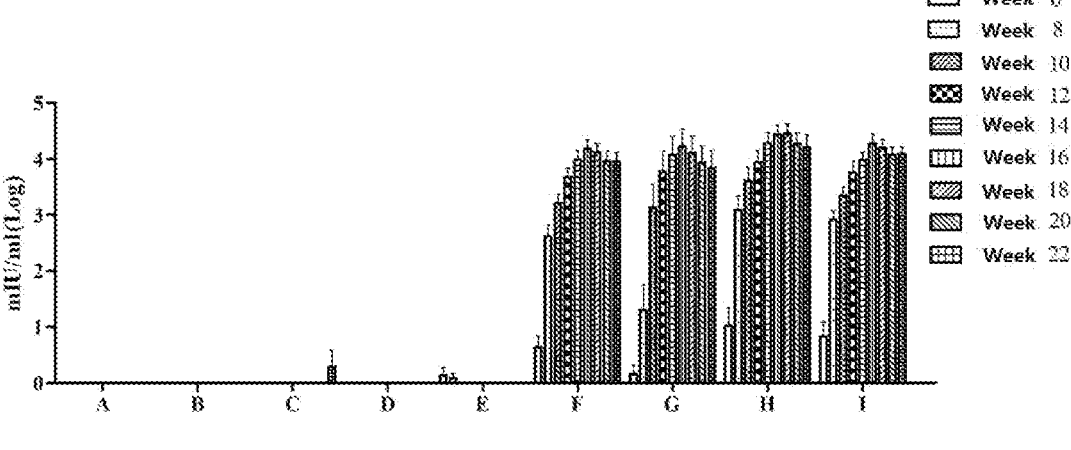
FIG. 8 shows the effects of the hepatitis B vaccines containing the immunostimulatory composition of the present invention on the level of HBsAb in serum.

2. Analysis of results (FIG. 8): Group H vaccine containing the immunostimulator began to generate HBsAb (>10 mIU/ml) after the second immunization (Week 6), and the level of HBsAb showed a trend of continuous increase as the number of immunizations increased, and the trend of increase was significantly superior to those of the CpG group alone (Group F) and the QS-21 group alone (Group G). Two weeks after the end of immunization (Week 16), the HBsAb level was close to saturation, reaching an HBsAb level of 4.0 logs, i.e. about 10000 mIU/ml. The antibody level generated was also significantly superior to that of the dual adjuvant control (Group I).

Example 8 Evaluation of Cellular Immune Effects of Hepatitis B Vaccines

1. Detection steps: following Example 2; and the experimental grouping is shown in Table 6.

2. Evaluation indicators: if the spot number of control well ≤5 SFC and the spot number of sample well ≥10 SFC, it will be determined as positive; if 5 SFC ≤ the spot number of control well ≤10 SFC, and the spot number of sample well/the spot number of control well ≥2, it will be determined as positive; and if the spot number of control well ≥10 SFC, and the spot number of sample well/the spot number of control well ≥3, it will be determined as positive.

TABLE 6

Positive conversion rates of HBsAg- and HBcAg-specific IFN-γ secreted by spleen cells

| Group | Number (animals) | Positive conversion rate (%) | |
|---|---|---|---|
| | | HBsAg | HBcAg |
| A | 9 | 11.1 | 11.1 |
| B | 9 | 0 | 11.1 |
| C | 8 | 0 | 0 |
| D | 8 | 12.5 | 12.5 |
| E | 9 | 37.5 | 12.5 |
| F | 9 | 100 | 100 |
| G | 8 | 100 | 100 |
| H | 8 | 100 | 100 |
| I | 8 | 100 | 100 |

Figure 9:
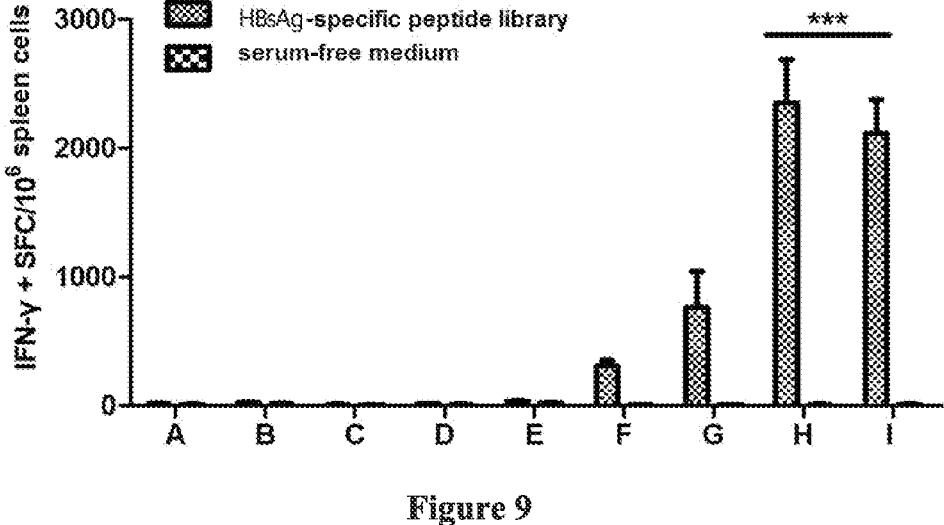
FIG. 9 shows the effects of the hepatitis B vaccines containing the immunostimulatory composition of the present invention on the secretion level of HBsAg antigen-specific IFN-$\gamma$.
Figure 10:
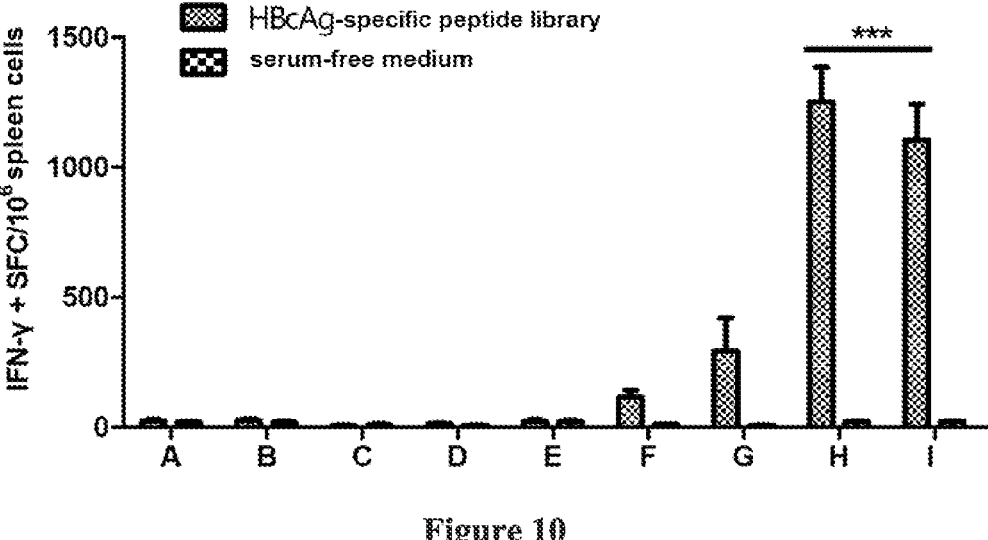
FIG. 10 shows the effects of the hepatitis B vaccines containing the immunostimulatory composition of the present invention on the secretion level of HBcAg antigen-specific IFN-$\gamma$.

3. Experimental results:

Detection results of cellular immune level: the results of ELISPOT spot are shown in FIGS. 9 and 10, and the analysis results show that the positive conversion rates of HBsAg-specific IFN-γ were 100% and the positive conversion rates of HBcAg-specific IFN-γ were 100% for Groups F-I. Group H vaccine containing the immunostimulator could induce higher production levels of HBsAg- and HBcAg-specific IFN-γ, greater than 2350 SFC/$10^6$ spleen cells and greater than 1250 SFC/$10^6$ spleen cells respectively, with significant differences compared to the CpG group alone (Group F) and the QS-21 group alone (Group G). The production levels of HBsAg- and HBcAg-specific IFN-γ induced by the dual adjuvant control (Group I) were about 1630 SFC/$10^6$ spleen cells and 750 SFC/$10^6$ spleen cells, which were significantly lower than those induced by Group H.

Example 9 Detection of HBsA2- and HBcA2-Specific Antibodies in Serum Induced by Pharmaceutical Compositions 1. Detection steps: a 96-well ELISA plate was coated with the purified HBsAg and HBcAg to form solid phase antigens. After blocking treatment, the serum to be detected was diluted serially at a certain initial dilution, and multiple dilutions were set. The serially diluted serum samples were added to the 96-well ELISA plate, and then bond to HRP-labeled anti-IgG/IgG 1/IgG 2a antibody to form an antigen-antibody (serum)-enzyme labeled antibody complexes. Finally, the substrate TMB was added for color development, and the absorbance (OD value) at 450 nm was measured with a microplate reader. The shade of developed color was positively correlated with the levels of HBsAg- and HBcAg-specific antibodies IgG/IgG 1/IgG 2a in the samples to be detected. The determination of antibody titers was performed by fitting the relationship curve of "absorbance OD value-dilution factor of serum sample (Log)".

2. Analysis of results:

1) Detection results of HBsAb IgG antibody and subtypes thereof in serum: An ELISA method was used to detect the levels of HBsAb IgG antibody and subtypes thereof in the mouse serum of each group at different time. As shown in FIG. 11, Group H vaccine containing the immunostimulator generated a higher titer of anti-HBsAg-specific IgG/IgG 1/IgG 2a antibody, and with the increase of immunization number, the antibody level continued to increase, and at the sixth immunization (Week 14), the antibody level approached saturation, and the specific antibody titer could reach more than 5.4 log. No specific antibodies were detected in Groups A-D. Although Groups E-G generated a certain level of HBsAg-specific IgG/IgG 1/IgG 2a antibody, the level of antibody was significantly lower than that in Group H. The levels of anti-HBsAg-specific IgG antibody and IgG 2a antibody generated in the dual adjuvant control (Group I) were significantly lower than those in Group H.

2) Detection results of HBcAb IgG antibody and subtypes thereof in serum:

An ELISA method was used to detect the levels of HBcAb IgG antibody and subtypes thereof in the mouse serum of each group at different time. As shown in FIG. 12, Group H vaccine containing the immunostimulator generated a higher titer of anti-HBcAg-specific IgG/IgG 1/IgG 2a antibody, and purchased from Hubei Yunmei Technology Co. Ltd.); Iscom adjuvant (purchased from Shanghai Xiyuan Biotechnology Co. Ltd.).

3) The HBsAg stock solution and HBcAg stock solution were diluted to 200 μg/ml and 100 μg/ml respectively, using a PBS solution (purchased from Hyclone), each of saponins was diluted to 50 μg/ml, and CpG T1 was dissolved and diluted to 100 μg/ml using the PBS solution, for the next step. 3. Experimental grouping: see Table 7. The dosage for each injection was 100 μL/mice, and Group A was the negative control (the PBS solution, 100 μL/mouse).

4. Experimental steps: following Example 2.

5. Experimental results: the results of ELISPOT spot are shown in FIG. 13 and FIG. 14. The results show that use of CpG T1 in combination with each of saponins resulted in a high-efficiency synergistic effect, and the induced production levels of HBsAg- and HBcAg-specific IFN-γ were significantly higher than those induced by the combinations of other CpGs and saponins, wherein QS21 had the best effect.

TABLE 7

| | | Component (μg/mouse) | | | | | | | | |
|---|---|---|---|---|---|---|---|---|---|---|
| Group | Number (animals) | HBs Ag | HBc Ag | CpG T1 | QS-21 | Ginsenoside Rg1 | Platycodin D | Astragalin A | Iscom adjuvant | CpG 7909 |
| Control | 5 | | | | | | | | | |
| Antigen | 5 | 20 | 10 | | | | | | | |
| QS-21 | 5 | 20 | 10 | 10 | 5 | | | | | |
| Ginsenoside Rg1 | 5 | 20 | 10 | 10 | | 5 | | | | |
| Platycodin D | 5 | 20 | 10 | 10 | | | 5 | | | |
| Astragalin A | 5 | 20 | 10 | 10 | | | | 5 | | |
| Iscom adjuvant | 5 | 20 | 10 | 10 | | | | | 5 | |
| 7909 | 5 | 20 | 20 | | 5 | | | | | 10 |

<div style="text-align:center">Grouping of experimental animals</div> with the increase of immunization number, the antibody level continued to increase, and at the sixth immunization (Week 14), the antibody level approached saturation, and the specific antibody titer could reach more than 4.8 log. No specific antibodies were detected in Groups A-D. Although Groups E-G generated a certain level of HBcAg-specific IgG/IgG 1/IgG 2a antibody, the level of antibody was significantly lower than that in Group H. And Group H was more inclined to Th1 pathway, and the specific antibody IgG 2a appeared a significant upward trend as shown in Figure D, reflecting that the vaccine of Group H could promote the subtype conversion of anti-HBcAg antibody, and the conversion efficiency was significantly higher than that of the dual adjuvant control (Group I).

Example 10 Effects of Different Saponins on Immune Effect of Pharmaceutical Composition 1. Experimental animals: C57BL/6(N) mice, male, 4 weeks old, 40 mice, Shanghai Lingchang Laboratory Animal Technology Co. Ltd.

2. Reagents and materials:

1) The HBsAg protein, HBcAg protein and CpG T1 were obtained from Example 1.

2) QS-21 (CAS. NO. A010-023, purchased from BRENNTAG); ginsenoside Rg1 (CAS: 22427-39-0, purchased from Nanjing Spring & Autumn Biological Engineering Co. Ltd.); astragalin A (CAS: 84687-43-4, purchased from Nanjing Spring & Autumn Biological Engineering Co. Ltd.); platycodin D (CAS: 58479-68-8, In conclusion, the pharmaceutical composition of the present invention uses a dual adjuvant combination. The CpGs T1~T3 of the present invention show a high-efficiency synergistic effect with various adjuvants, especially QS-21, and can mediate a stronger immune response, compared with a single adjuvant or the combinations of other CPG adjuvants and QS21. The pharmaceutical composition containing the immunostimulatory composition has significant advantages, exhibits high-efficiency immunotherapeutic effects, and has high clinical application value and broad market prospect.

Although the present invention has been described in detail above, those skilled in the art will appreciate that various modifications and variations can be made to the present invention without departing from the spirit and scope of the present invention. The right scope of the present invention is not to be limited by the foregoing detailed description, and the modifications and variations are intended to fall within the scope of the claims. While only examples of specific embodiments of the present invention have been described above, it will be appreciated by those skilled in the art that the foregoing is illustrative only and that the protection scope of the present invention is to be defined by the appended claims. Various variations and modifications can be made by those skilled in the art in the embodiments without departing from the principle and essence of the present invention, but such changes or modifications should all fall within the protection scope of the present invention.

The invention claimed is:

1. A pharmaceutical composition comprising:

i) a hepatitis B surface antigen, an active fragment of the antigen, a variant of the antigen, or a mixture of at least two of them;

ii) a hepatitis B core antigen, an active fragment of the antigen, a variant of the antigen, or a mixture of at least two of them; and iii) an immunostimulatory composition comprising a saponin and a CpG oligodeoxynucleotide, or consisting of an adjuvant comprising a saponin and a CpG oligodeoxynucleotide, wherein the sequence of the CpG oligodeoxynucleotide is any one selected from: CpG T1: TCG TTC GTT CGT TCG TTC GTT (SEQ ID NO: 6); CpG T2: TCG TTC GTT CGT TCG TTC GTT CGT T (SEQ ID NO: 7); and CpG T3: TCG TCG TCG TCG TCG TCG (SEQ ID NO: 8), and the saponin is QS-21.

2. The pharmaceutical composition according to claim 1, wherein the CpG oligodeoxynucleotide comprises a phosphorothioate linkage.

3. The pharmaceutical composition according to claim 1, wherein the CpG oligodeoxynucleotide is a thio-oligodeoxynucleotide.

4. The pharmaceutical composition according to claim 1, wherein the CpG oligodeoxynucleotide is a perthio-oligodeoxynucleotide.

5. The pharmaceutical composition according to claim 1, wherein the weight ratio of the CpG oligodeoxynucleotide to the saponin is 1~40:0.1~2.

6. The pharmaceutical composition according to claim 1, wherein the weight ratio of the CpG oligodeoxynucleotide to the saponin is 2:1.

7. The pharmaceutical composition according to claim 1, wherein the Hepatitis B surface antigen comprises or consists of the sequence as shown by SEQ ID NO: 1, and the Hepatitis B core antigen comprises or consists of the sequence as shown by SEQ ID NO: 2.

8. The pharmaceutical composition according to claim 1, wherein the active fragment of the hepatitis B core antigen comprises or consists of consecutive amino acids from position 1 to position X of SEQ ID NO: 2, wherein X is an integer between 149 and 183.

9. The pharmaceutical composition according to claim 8, wherein the active fragment of the hepatitis B core antigen comprises or consists of consecutive amino acids from position 1 to position X of SEQ ID NO: 2, wherein X is an integer between 152 and 183.

10. The pharmaceutical composition according to claim 1, wherein the weight ratio among Components i), ii) and iii) in the pharmaceutical composition is 4:2:1.1~42.

11. The pharmaceutical composition according to claim 1, wherein the weight ratio among Components i), ii) and iii) in the pharmaceutical composition is 4:2:3.

12. The pharmaceutical composition according to claim 1, wherein the pharmaceutical composition further comprises:

iv) a pharmaceutically acceptable carrier.

13. A hepatitis B prophylactic or B therapeutic vaccine, comprising the pharmaceutical composition of claim 1.

14. A method for preventing and/or treating a hepatitis B virus infection and/or a hepatitis B virus mediated disease, comprising administering to a subject in need thereof a prophylactically and/or therapeutically effective amount of the pharmaceutical composition according to claim 1.

15. The method according to claim 14, wherein the hepatitis B virus infection and/or the hepatitis B virus mediated disease is selected from the group consisting of cirrhosis and liver cancer.

16. A method for generating a humoral immune response and/or a cellular immune response against hepatitis B virus in a subject, comprising administering to a subject in need thereof an effective amount of the pharmaceutical composition of claim 1.

17. A method for switching the subtype of hepatitis B core antibody in a subject, comprising administering to a subject in need thereof an effective amount of the pharmaceutical composition of claim 1.

18. A method for breaking through the immune tolerance of hepatitis B virus in a subject, comprising administering to a subject in need thereof an effective amount of the pharmaceutical composition of claim 1.

* * * * *